United States Patent
Muzio et al.

(10) Patent No.: US 7,635,593 B2
(45) Date of Patent: Dec. 22, 2009

(54) IN-LINE LOCALIZED MONITORING OF CATALYST ACTIVITY IN SELECTIVE CATALYTIC $NO_x$ REDUCTION SYSTEMS

(75) Inventors: Lawrence J. Muzio, Laguna Niguel, CA (US); Randall A. Smith, Huntington Beach, CA (US)

(73) Assignee: Fossil Energy Research Corp. (FERCO), Laguna Hills, CA (US)

( * ) Notice: Subject to any disclaimer, the term of this patent is extended or adjusted under 35 U.S.C. 154(b) by 912 days.

(21) Appl. No.: 11/112,667

(22) Filed: Apr. 21, 2005

(65) Prior Publication Data
US 2005/0255605 A1    Nov. 17, 2005

Related U.S. Application Data

(60) Provisional application No. 60/571,100, filed on May 14, 2004.

(51) Int. Cl.
| | |
|---|---|
| *G01N 31/10* | (2006.01) |
| *F01N 3/10* | (2006.01) |
| *B01D 53/30* | (2006.01) |
| *B01D 53/56* | (2006.01) |

(52) U.S. Cl. .............. 436/37; 60/274; 60/276; 422/110; 422/111; 422/130; 422/171; 422/172; 436/106; 436/113; 436/116; 436/117; 436/118; 436/127; 436/136; 436/159

(58) Field of Classification Search .......... 422/129, 422/130, 105, 110–111, 171–172; 436/37, 436/106, 113, 116–118, 127, 136, 159; 60/274, 60/276; 110/345

See application file for complete search history.

(56) References Cited

U.S. PATENT DOCUMENTS 5,237,939 A  *  8/1993  Spokoyny et al. ........... 110/345

(Continued)

FOREIGN PATENT DOCUMENTS

JP      55-24535      *  2/1980

(Continued)

OTHER PUBLICATIONS

Becker, Bill et al.; "B&W's $NO_x$ Reduction Systems and Equipment at Moss Landing Power Plant"; 2000, *ICAC $No_x$ Forum*, 5 pages.

(Continued)

*Primary Examiner*—Arlen Soderquist
(74) *Attorney, Agent, or Firm*—Townsend and Townsend and Crew LLP.; M. Henry Heines (57) ABSTRACT

Localized catalyst activity in an SCR unit for controlling emissions from a boiler, power plant, or any facility that generates $NO_x$-containing flue gases is monitored by one or more modules that operate on-line without disrupting the normal operation of the facility. Each module is positioned over a designated lateral area of one of the catalyst beds in the SCR unit, and supplies ammonia, urea, or other suitable reductant to the catalyst in the designated area at a rate that produces an excess of the reductant over $NO_x$ on a molar basis through the designated area. Sampling probes upstream and downstream of the designated area draw samples of the gas stream for $NO_x$ analysis, and the catalyst activity is determined from the difference in $NO_x$ levels between the two probes.

39 Claims, 4 Drawing Sheets

U.S. PATENT DOCUMENTS

| | | | |
|---|---|---|---|
| 5,584,172 A * | 12/1996 | Oguchi et al. | 60/39.5 |
| 5,643,536 A * | 7/1997 | Schmelz | 422/105 |
| 6,017,503 A * | 1/2000 | Kato et al. | 423/235 |
| 6,044,689 A * | 4/2000 | Yoshida et al. | 73/31.03 |
| 6,245,134 B1 | 6/2001 | Sandler | |
| 6,510,820 B1 | 1/2003 | McDonald | |
| 6,516,607 B1 * | 2/2003 | Bruck et al. | 60/274 |
| 6,546,720 B2 * | 4/2003 | van Nieuwstadt | 60/286 |
| 6,548,033 B2 | 4/2003 | Ganeshan | |
| 6,662,553 B2 | 12/2003 | Patchett et al. | |
| 6,694,900 B2 | 2/2004 | Lissianski et al. | |
| 6,808,692 B2 | 10/2004 | Oehr | |
| 6,837,702 B1 | 1/2005 | Shelor et al. | |
| 6,996,975 B2 * | 2/2006 | Radhamohan et al. | 60/286 |
| 7,056,478 B1 * | 6/2006 | Rini et al. | 422/171 |
| 2006/0099110 A1 * | 5/2006 | Shirakura | 422/62 |

FOREIGN PATENT DOCUMENTS

| | | | |
|---|---|---|---|
| JP | 04-338217 | * | 11/1992 |
| JP | 2004-66228 | * | 3/2008 |
| JP | 2002-162393 | * | 6/2008 |
| JP | 2003-290630 | * | 10/2008 |

OTHER PUBLICATIONS

Muzio, Lawrence J.; "In Situ Test Reactor"; 2000, *Fossil Energy Research Corporation*, 7 pages.

Nischt, Walter et al.; "Update of Selective Catalytic Reduction Retrofit on a 675 MW Boiler at AES Somerset"; 2000, *ASME International Joint Power Generation Conference*, 8 pages.

Sun, William H. et al.; "Small Scale Test Results from New Selective Catalytic NOx Reduction Process Using Urea"; 2001, *Mega Symposium*, 6 pages.

"VGB Guideline: Guideline for the Testing of Denox Catalysts"; 1998 *VGB Technical Association of Large Plant Operators*, 32 pages.

* cited by examiner

IN-LINE LOCALIZED MONITORING OF CATALYST ACTIVITY IN SELECTIVE CATALYTIC $NO_x$ REDUCTION SYSTEMS

CROSS-REFERENCES TO RELATED APPLICATIONS

This application is related to U.S. Provisional Patent Application No. 60/571,100, filed May 14, 2004, and claims all benefits legally capable of being offered by the provisional patent application. The entire contents of the provisional patent application are incorporated herein by reference.

STATEMENT AS TO RIGHTS TO INVENTIONS MADE UNDER FEDERALLY SPONSORED RESEARCH OR DEVELOPMENT

This invention was made with Government support under contract no. DE-FC26-05NT42298 awarded by the Department of Energy. The government has certain rights in this invention.

BACKGROUND OF THE INVENTION

1. Field of the Invention

This invention resides in the field of $NO_x$ emissions from combustion facilities, and methods and plant equipment using selective catalytic reduction (SCR) for controlling and reducing the emissions.

2. Description of the Prior Art

A widely used process for the reduction of $NO_x$ emissions from coal-fired utility boilers and in combustion flue gases in general is the process known as selective catalytic $NO_x$ reduction (SCR). In this process, the $NO_x$ in the flue gas is reacted with oxygen and ammonia over a solid catalyst which is either a metal such as titanium, vanadium or platinum, or a zeolite or a ceramic, to reduce the nitrogen in $NO_x$ to molecular nitrogen with water as a by-product. The utility industry has invested billions of dollars in SCR units, and these units collectively utilize a volume of catalyst that is on the order of 200,000 $m^2$.

The performance of an SCR unit, as measured by the change in $NO_x$ concentration across the unit ($\Delta NO_x$), depends on the catalyst activity and the area velocity $A_v$ of the unit according to the relation $$\Delta NO_x = 1 - e^{-K/A_v} \quad (1)$$

where K is the catalyst activity and $A_v$ is defined by the relation $$A_v = \frac{Q}{VA_s} \quad (2)$$

where Q is the flue gas flow rate through the unit, V is the bulk catalyst volume, and $A_s$ is the surface area of the catalyst per unit volume of the catalyst. Contributing to the catalyst activity K are such factors as the mass transfer coefficient, the kinetic rate constant and various geometric factors. The typical SCR catalyst is rated by its vendor with an initial catalyst activity $K_o$. The catalyst activity and hence the $NO_x$ reduction potential of the unit decrease gradually over time as the catalyst is subjected to macro- and micropore diffusion, absorption, desorption, chemical reactions involving the catalyst itself, and catalyst poisons. To maintain the desired level of $NO_x$ reduction, the rate of ammonia injection must then be increased to compensate for the decrease in catalyst activity. This in turn results in greater amounts of unreacted ammonia leaving the unit (the "ammonia slip") and therefore greater cost in operating the unit, a greater risk of pollution, and possible adverse impacts on downstream equipment. Catalyst degradation is further complicated by the fact that in large catalytic reactors the catalyst is deployed in two or more distinct and separated layers, with different layers tending to degrade at different rates. Even in a single layer, the catalyst can undergo different degradation rates at different locations in the layer. As the catalyst continues to degrade, replacement or regeneration is eventually necessary. Typically, one-third to one-fourth of the catalyst is replaced or regenerated approximately every 15,000 to 25,000 hours of continuous use.

A well-run boiler or combustion facility will have a catalyst management procedure for the SCR unit that will allow the facility to comply with the regulatory requirements for $NO_x$ and $NH_3$ emissions, and yet conform to the outage schedule for the facility. Periodic monitoring of the catalyst provides the most efficient use of the catalyst and allows operators to maintain the facility in compliance with the regulations. Monitoring methods that are in current use introduce inefficiencies of their own, however.

One of these methods is by monitoring the ammonia slip. Another is by monitoring the ammonia content of the fly ash. Either method provides only an indirect indication of the catalyst activity, and only a gross or overall indication of any loss in activity. These methods will not differentiate between situations in which all catalyst layers are losing activity at approximately the same rate from those in which upstream layers are losing activity at a greater rate than those downstream. A further difficulty is that increases in the ammonia slip or in the ammonia content of the fly ash may be the result of factors other than catalyst activity, such as an ammonia injection grid that is not properly adjusted or any other irregularity in the ammonia injection system.

Another monitoring method is that in which samples of catalyst are removed from the reactor and transferred to a laboratory for direct determinations of the catalyst activity or the activity ratio $K/K_o$. This can also be done with catalyst coupons retained in the reactor in a special removable holder. Removal of the samples or coupons however usually requires that the unit be taken off-line. Unless the unit is expressly shut down for the sampling, the time interval between sampling opportunities will be dictated by the outage schedule of the unit rather than concerns over the catalyst activity and can be very long. For those units operating on a schedule that is designed to accommodate the ozone season, for example, outages may occur as seldom as once or twice a year. For units operating year-round, the sampling frequency may be even lower, such as once every other year. A further problem with the withdrawal of catalyst samples is that the analyses of these samples provide no information regarding how any observed decrease in catalyst activity occurred, i.e., whether the decrease occurred slowly and gradually over time or by a step change resulting from a boiler upset, a fuel change, or some other occurrence not related to the SCR unit itself.

SUMMARY OF THE INVENTION

The present invention resides in modules for monitoring catalytic activity on a localized basis in an SCR unit, methods of on-line monitoring of SCR catalyst activity utilizing such modules, and SCR units that contain such modules, all either reducing or eliminating the deficiencies of the prior art methods. Each module is sized to extend over a lateral area of a catalyst layer that is small relative to the full area of the layer as well as the cross section of the gas flow stream through the SCR reactor and includes a pair of sampling probes for drawing samples from the gas stream traversing the area both upstream and downstream of the catalyst plus a reductant supply probe for directing a fresh reductant stream to the area. Suitable reductants are ammonia gas, a mixture of ammonia and air, and aqueous urea. The module is constructed and mounted in such a way that it does not disrupt, block, or interfere with the bulk flow through the SCR unit, and can be activated and deactivated at will without shutting down the unit. The reductant is fed through the reductant supply probe at a rate sufficient to achieve an excess (on a mole basis) of reductant over the $NO_x$ entering the catalyst area that the module is positioned over, while the samples from the sampling probes are directed to analyzers and a data processing unit that determine the $NO_x$ levels in each probe and calculate the catalyst activity from the difference in $NO_x$ levels and the area flow rate according to the following relation, which is derived from Equation (1) above:

$$K = A_v \ln(1 - \Delta NO_x) \quad (3)$$

In preferred embodiments of the invention, the module further includes a temperature sensor and, in certain embodiments, a gas velocity sensor. Further modules within the scope of the invention also include an air inlet for blowing soot from the catalyst in the module area, and miscellaneous flow control components such as an ammonia injection grid when ammonia is used as the reductant, the grid is sized to distribute the added ammonia over the catalyst in the module area, a static mixer to promote uniform mixing of the added reductant into the gas stream in the module area, and lateral barriers or shrouds sized to surround the catalyst to prevent the divergence of gas flows from the catalyst area to adjacent areas or vice versa.

In preferred embodiments as well, the SCR unit contains two or more, and in general a plurality, of these test modules distributed at strategic locations across the width of a single catalyst layer or among different catalyst layers, or both, to provide localized analyses at different locations. With a plurality of modules, a common source of reductant and a common analyzer for all modules can be used, with appropriate switching valves for supplying reductant and drawing samples from individual modules in sequence, either periodically or at the will of the operator. In still further embodiments, the modules are mounted on a movable support permitting lateral movement or re-positioning of individual modules to achieve localized activity information at various locations from a single module.

The modules, methods and systems of the present invention permit the monitoring of the catalyst activity to be performed independently of any outage schedule for the SCR unit or the facility as a whole and without interfering with the operation of the unit or the facility. Further advantages, embodiments, and objects of the invention will be apparent from the description that follows.

DETAILED DESCRIPTION OF THE INVENTION AND PREFERRED EMBODIMENTS

The terms "reactor" and "SCR unit" are used interchangeably to refer to a continuous flow-through reactor in which an $NO_x$-containing gas is combined with ammonia and contacted with catalyst to undergo any of various reactions in which the nitrogen in the $NO_x$ is reduced to molecular nitrogen.

The term "solid catalyst layer" as used herein denotes a body of catalyst in solid form, either as a bed of catalyst particles or a unitary piece of solid catalytic material, that is immobile and substantially flat, with lateral dimensions that significantly exceed its thickness, and contains pores or though-passages that allow the $NO_x$-containing gas to flow through the body of catalyst in intimate contact with the catalyst surface area. When the catalyst is in particulate form, the particles can be retained on a tray or mesh support, and when the catalyst is a unitary block of material such as a honeycomb ceramic block or a stack of plates with corrugated profiles, the block or stack of plates can be supported in the reactor by beams, support grids, or other conventional construction components. Typically, the catalyst layer will span the cross section of the SCR unit, forcing the gas stream to pass through the catalyst layer in intimate contact with the catalyst and preventing bypass.

The terms "lateral," "lateral area," and "laterally delineated section" as used herein refer to spatial regions of the internal volume of the reactor, and denote the dimensions or the extremities or boundaries of these regions along the x- and y-axes, i.e., the axes that are transverse to the direction of gas flow through the reactor (which is referred to herein as the z-axis). When used in reference to a section of a catalyst layer, these terms refer to the lateral dimensions of the section rather than the thickness of the layer. While the spatial regions referred to will generally be occupied by catalyst, the word "area" when included in these terms does not refer to the surface area of the catalyst.

The terms "upstream" and "downstream" as used herein refer to locations relative to the direction of gas flow through the reactor.

The term "substantially parallel flow direction" as used herein in reference to a gas flow stream denotes a stream that is substantially both non-diverging and non-converging along its direction of flow.

The term "ammonia gas" is used herein to include both undiluted ammonia and ammonia mixed with air or an inert gas such as nitrogen. In the preferred practice of this invention, the ammonia will be fed as a mixture with air, at proportions ranging from about 1% ammonia by volume to about 80% ammonia by volume, or more preferably from about 5% to about 60%.

The term "aqueous urea" is used herein to mean urea dissolved in water. In the preferred use of aqueous urea in the practice of this invention, the aqueous urea will contain from about 1% to about 50% urea by weight, or more preferably from about 2% to about 25% by weight, and will be sprayed into the flue gas through an atomizer.

The term "selectively strike" as used herein in reference to an air or gas stream directed to a section of the catalyst bed denotes that the entire stream is confined to the area with the lateral extremities of the section and does not diverge outside those extremities.

The terms "a" and "an" as used herein mean "one or more," and are therefore broader in scope than the term "plurality."

While this invention is capable of implementation in a wide range of constructions, applications, and embodiments, a thorough understanding will be gained by a detailed examination of a specific embodiment. Such an embodiment is shown in the drawings and explained below.

Figure 1:
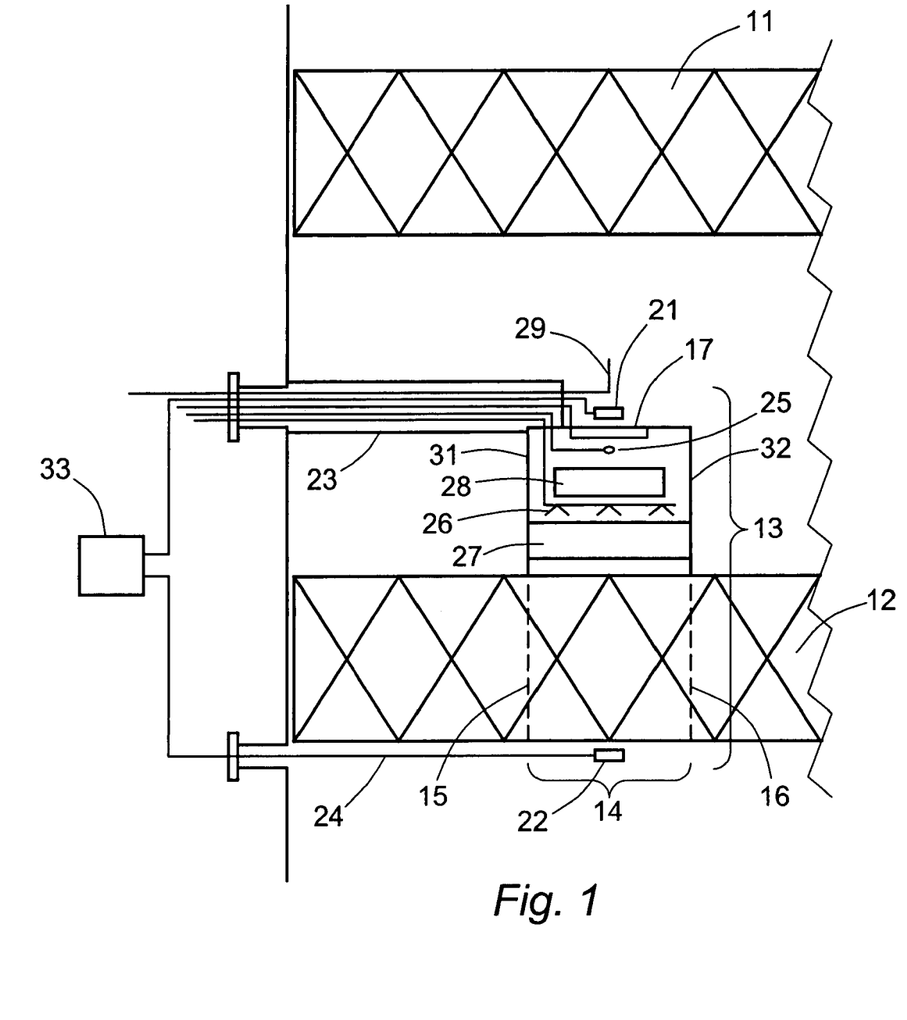
FIG. 1 is a vertical cross section of a portion of a vertical flow-through SCR unit containing a catalyst monitoring module in accordance with the present invention.

FIG. 1 represents a partial cross section of an SCR unit taken along the direction of gas flow through the unit (the z-axis), showing one test module in accordance with the invention. In this cross section, two catalyst layers are shown, the first 11 positioned upstream of the second 12 and both spanning the entire cross section of the unit. The flow direction of $NO_x$-containing gas through this unit is from the top down in the view shown in the Figure. The gas thus passes through the catalyst in the first layer 11 before proceeding to the catalyst in the second layer 12. A single module 13 is positioned to monitor the catalyst activity in a laterally designated section 14 of the second catalyst layer 12. The section 14 has lateral extremities, of which only two opposing sides 15, 16 are visible in this cross section, that define an area that is a relatively small portion of the entire cross section of the unit. In preferred applications, the lateral area of the section ranges from about $0.1\ m^2$ to about $1\ m^2$, and more preferably from about $0.2\ m^2$ to about $0.5\ m^2$. The ratio of this area to the cross section area of the entire reactor is preferably about 0.25 or less, and more preferably about 0.1 or less. The shape of the module section area 14 can be square, circular, or any practical or convenient shape, and will be determined by the flow configurations emerging from the ammonia inlet probe and any lateral barriers (discussed below) that are included in the module. The dimensions, area ratio, and shape are not critical to the invention and can vary widely.

The ammonia supply probe 17 is a component of the module, and in the embodiment shown in the Figure the probe incorporates an ammonia injection grid and is positioned directly upstream of (above) the designated area 14 of the catalyst bed in which the activity determination is to be performed. The probe and grid are selected and arranged to produce an ammonia stream that selectively strikes the designated area 14 and preferably strikes substantially the entire area. The height of the probe and grid above the catalyst bed will vary depending on the grid configuration and any other components included in the module. In most cases, a height of from about 1 foot to about 8 feet (0.3 to 2.4 meters), and preferably from about 2 feet to about 6 feet (0.6 to 1.8 meters), will provide the best results, depending on any additional components that might be placed between the grid and the catalyst surface.

The inlet sampling probe 21 is likewise positioned upstream of the designated area 14 of the catalyst bed, and the outlet sampling probe 22 is positioned downstream of the designated area. In this embodiment, the inlet sampling probe 21 is positioned upstream of the ammonia injection grid 17 to assure that the analysis of the sample drawn through this probe is representative of the gas stream flowing through the unit at that level. Both sampling probes preferably include a filter incorporated into the probe to prevent soot or solid matter in general from entering the lines leading to the analyzer(s).

The mounting structures 23, 24 for the ammonia supply probe and grid 17 and for the inlet and outlet sampling probes 21, 22 and all other components of the module are any conventional supports, beams, frames, brackets, or the like that will secure the components in place without disrupting or interfering with the gas flow through the SCR unit as a whole. The mounting structures may range from simple angle irons to which the components are bolted or welded in fixed positions, to rails along which the components are slid so that they can be positioned at different locations along a particular catalyst layer. The mounting structures can be combined to make the module a unitary piece of equipment with all components attached, or they can be individual beams or rails for individual components of the module. Accordingly, the module can be manufactured as a separate piece of equipment or constructed as part of the SCR unit itself from individual components.

Further components for optional, and in certain cases preferred, inclusion in a module of the present invention, as mentioned above, are a temperature sensor, a soot blower, a flow rectifier to guide the $NO_x$-containing gas entering the module into a substantially parallel flow direction, a static mixer downstream of the ammonia probe and ammonia injection grid to promote the uniform mixing of the ammonia with the gas flow stream, and a shroud or lateral enclosure wall as further assurance against lateral diffusion of gases or interfering materials between the catalyst area addressed by the module and adjacent catalyst areas. These optional components can be included individually or in any combination, and all can be mounted to module by conventional mounting fixtures.

In the embodiment shown in FIG. 1, the module includes a thermocouple 25 centered in the module and positioned above, i.e., upstream of, the catalyst area addressed the module. Optionally the thermocouple can be positioned on the downstream side of the catalyst area. Temperature sensors other than thermocouples can be used as well. Examples are thermistors, metallic resistive temperature devices (RTDs), infrared sensors, bimetallic devices, fluid-expansion devices, and change-of-state temperature sensors.

The module of FIG. 1 also includes a soot blower 26 which is an air injection inlet whose purpose is to clear the catalyst area 14 of ash particles that might obstruct the flow of gas through the catalyst area. Air is the most convenient, but the blower can utilize any gas that will not affect the catalyst.

A still further component shown in the module of FIG. 1 is a flow rectifier 27. The rectifier can be any arrangement of plates, tubes, or grid that guide the bulk gas flow toward the module in a parallel direction. The flow rectifier can be similar in design and construction to the flow rectifiers that are often used in SCR units as a whole but reduced in scale to the dimensions of the module. A further component shown in the Figure is a static mixer 28. Blade-type static mixers and helical static mixers are examples of mixers that are widely available from commercial suppliers to the chemical engineering industry. Other designs can be used as well. Here again, the appropriate static mixer will be one whose size matches the scale of the module. Also shown in the Figure is a flow measuring device 29 to measure the flue gas velocity approaching the catalyst. Conventional flow measuring devices can be used; examples are thermal anemometers and pitot tubes.

Also included as part of the module of FIG. 1 is the shroud referred to above, in the form of sheet metal walls of which only two 31, 32 are visible. These walls enclose the perimeter of the space above the catalyst area 14. A still further component is a portable $NO_x$ analyzer 33 that is shown mounted to the flowlines extending from the inlet and outlet sampling probes. Portable $NO_x$ analyzers are known in the industry and readily available from commercial suppliers. An example is the non-sampling type MEXA-720NOx Analyzer of Horiba Instruments Incorporated (Irvine, Calif. USA). Other $NO_x$ analyzers, portable and on-portable, can also be used and are discussed below.

Figure 2:
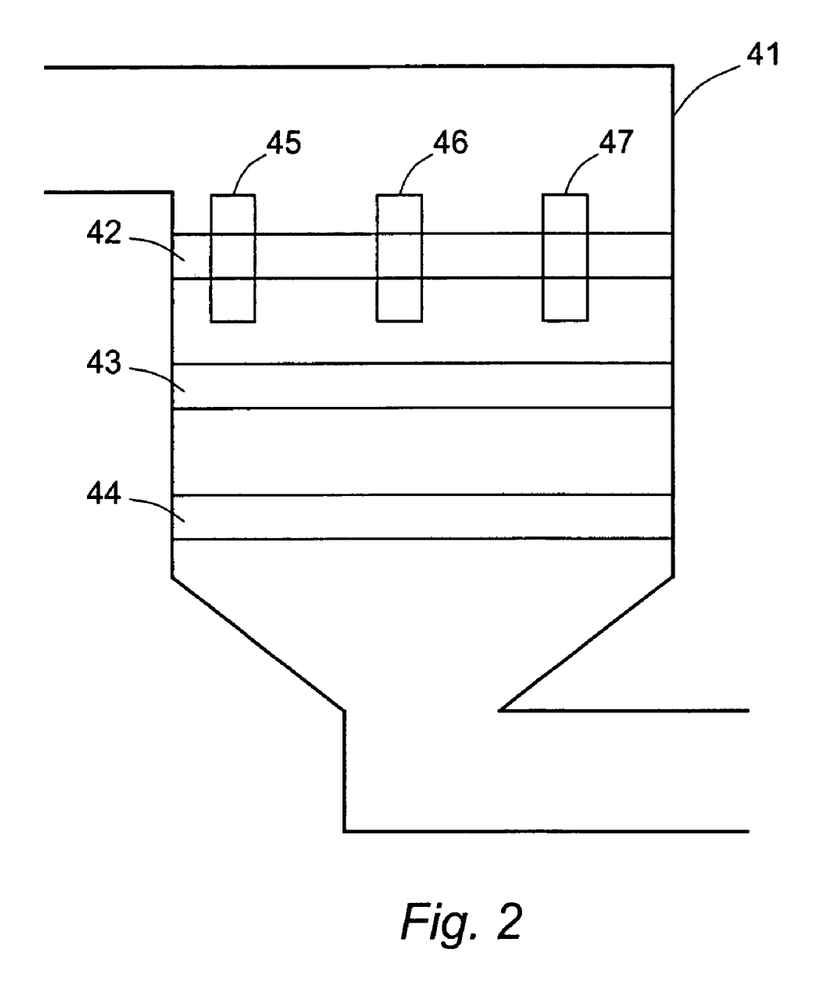
FIG. 2 is a vertical cross section of an entire flow-through SCR unit containing three catalyst layers and three catalyst monitoring modules in accordance with the present invention.
Figure 3:
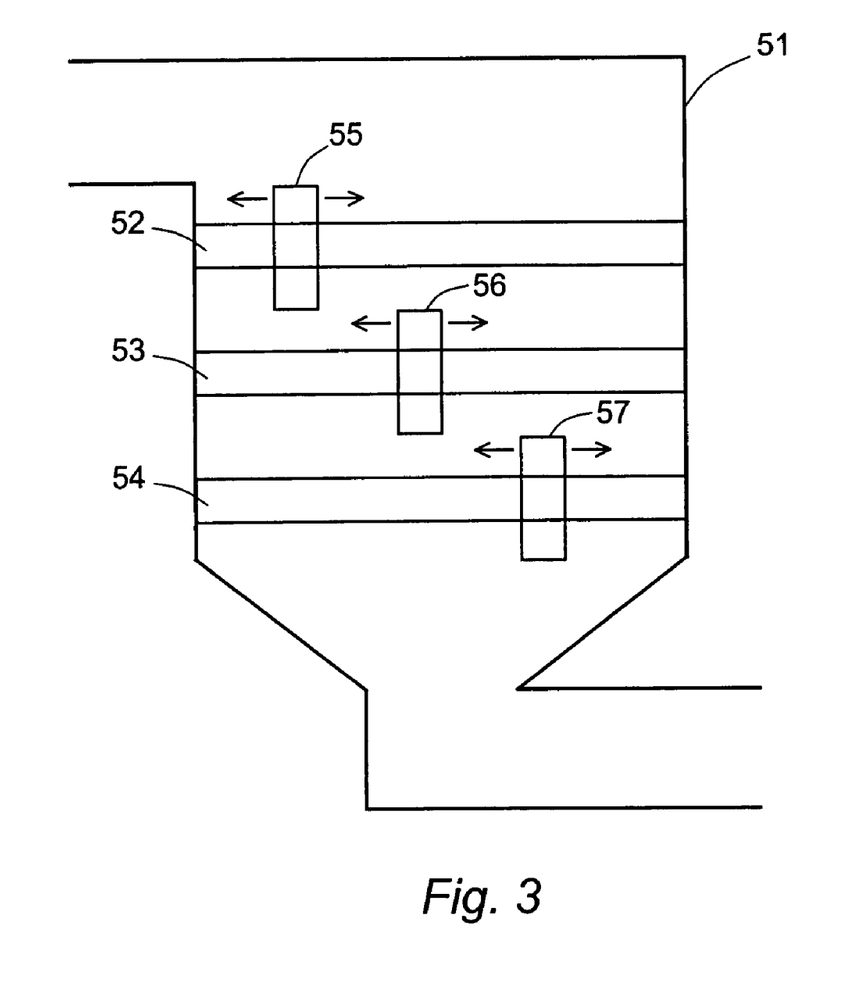
FIG. 3 is a vertical cross section of another flow-through SCR unit containing three catalyst layers and three catalyst monitoring modules in accordance with the present invention, in a configuration different from that shown in FIG. 2.

The number of modules used in a single SCR unit is not critical to the invention and can vary. Preferably, a plurality of modules are used so that localized catalyst activity can be monitored at different sites along the flow path of the gas being treated in the unit. Movable modules, as described above, can also serve to provide localized monitoring data over wide areas. Typical configurations of the catalyst layers in an SCR unit are shown in FIGS. 2 and 3, with different arrangements of modules. In FIG. 2, the SCR unit 41 has three layers 42, 43, 44 of catalyst, and three modules 45, 46, 47 distributed across a single layer. In FIG. 3, the SCR unit 51 likewise has three catalyst layers 52, 53, 54, and three modules 55, 56, 57 are shown, one in each layer. The modules in FIG. 3 are movable as indicated by the arrows, so that each can be placed at any location across the width of the catalyst bed that it is adjacent to.

The peripheral equipment and components used in association with the modules of the present invention are conventional components that are known in the boiler and power plant industry and readily available from commercial suppliers. The primary peripheral comments include pumps for drawing samples through the sample probes, flow controllers for the supply lines for ammonia and air, $NO_x$ analyzers, and, if desired, oxygen analyzers. For $NO_x$ analyses other than by the use of the portable analyzers mentioned above, chemiluminescence $NO_x$ analyzers are of particular interest. Examples are Brand-Gaus Chemiluminescence $NO_x$ Analyzers (Brand-Gaus, LLC, Pflugerville, Tex., USA), ECO PHYSICS Chemiluminescence $NO_x$ Analyzers (ECO PHYSICS, INC., Ann Arbor, Mich., USA), and Environmental Analytical Systems' Model 400 CLD and Model 400 HCLD Chemiluminescent $NO/NO_x$ Analyzers (Environmental Analytical Systems, Barry's Bay, Ontario, Canada). Analyzers for molecular oxygen are also included in certain embodiments of the invention for the purpose of detecting leaks in the sampling system. Examples of oxygen analyzers are the Series 800 Zirconia Oxygen Analyzer of Illinois Instruments, Inc. (Johnsburg, Ill., USA), the Integrated Type In Situ Zirconia Oxygen Analyzer Model ZR202G of Yokogawa Corporation of America (Newnan, Ga., USA), and the CGA351 Zirconia Oxygen Analyzer of GE Panametrics (Gymea, New South Wales, Australia).

Monitoring systems in accordance with this invention can be designed for manual operation or automated operation. Manually operated systems will be those with manually controlled sample pumps, manually controlled analyzers, and manual controls in general for energizing individual modules or positioning movable modules. An example of an automated system for six test modules in a single SCR unit is shown in FIG. 4.

Figure 4:
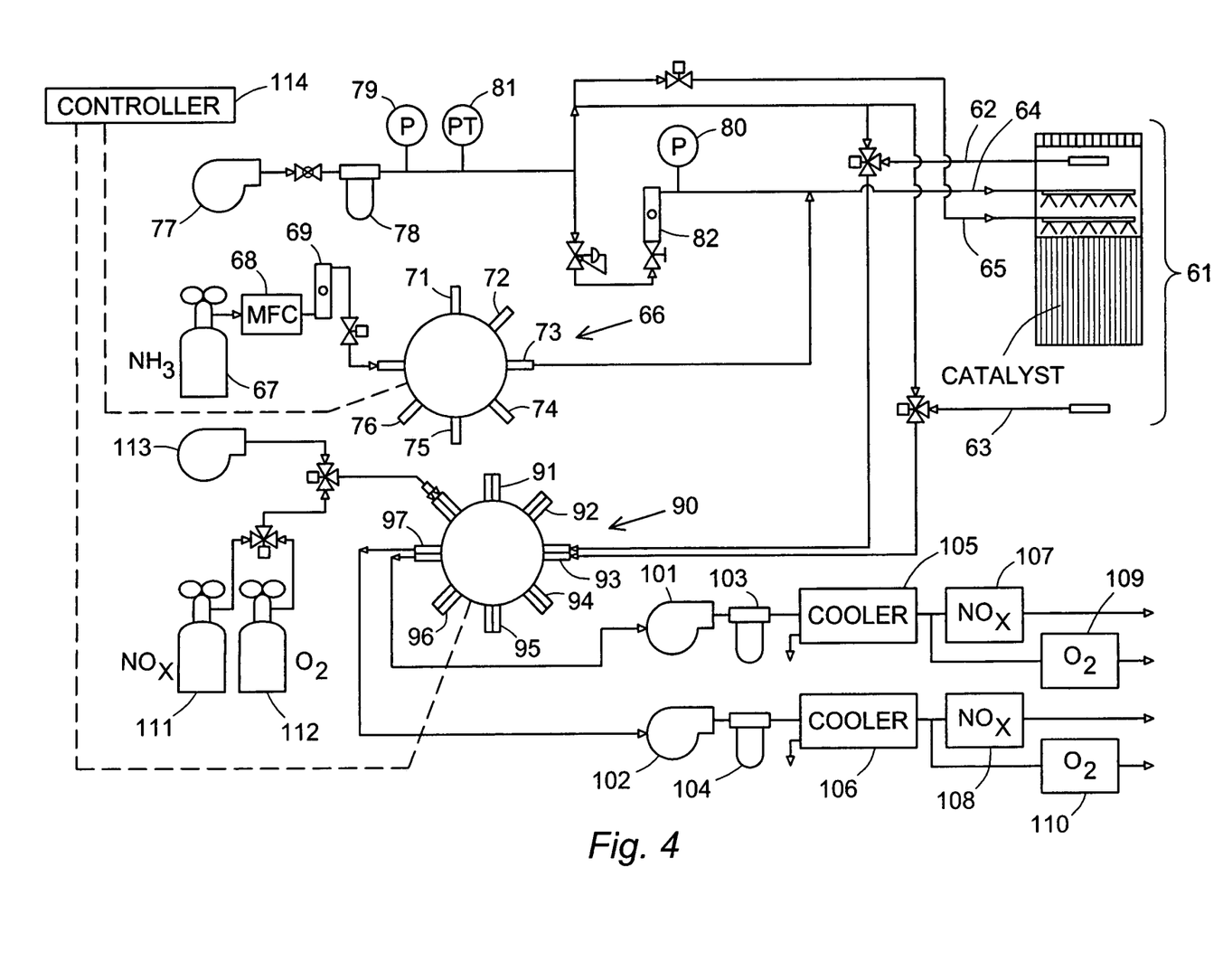
FIG. 4 is a process flow diagram of an automated system for monitoring catalyst activity at six locations in an SCR unit.

The system of FIG. 4 performs analyzes from each of the six modules in succession, one at a time. Only one module 61 of the six is shown. The flow lines to and from the module are an inlet sampling line 62 and an outlet sampling line 63 from the inlet and outlet sampling probes, respectively, an ammonia supply line 64, and an air supply line 65 for the soot blower. Two stepping valves control the selection of the module that is in use and the progression of the analysis from one module to the next. The first stepping valve 66 is supplied by a single source of anhydrous ammonia gas 67, whose flow rate is controlled by a mass flow controller 68, and measured by a flow meter 69. The stepping valve rotates between six outlet ports 71, 72, 73, 74, 75, 76, one for each of the six modules. Before reaching a module, the ammonia is combined with air from an air source such as a blower 77, which passes through a filter 78, pressure gauges 79, 80, a pressure transmitter 81, and a flow meter 82. The same air source feeds air to the air supply line 65 supplying the soot blower. The second stepping valve 90 receives gas stream samples from the inlet and outlet sampling lines 62, 63, respectively, through a pair of inlet ports that represent one of six pairs of inlet ports 91, 92, 93, 94, 95, 96, one for each of the six modules. A single pair of outlet ports 97 from the stepping valve leads to a single pair of sample pumps 101, 102, one pump for the inlet samples and the other for the outlet samples. The samples thus drawn pass through filters 103, 104 and moisture removers 105, 106 (such as for example thermoelectric coolers), and each sample stream is then passed through a $NO_x$ analyzer 107, 108 and an oxygen analyzer 109, 110. The outlets of the analyzers are open to vent. Supplies of $NO_x$ 111 and molecular oxygen 112 are connected to the system for use in calibrating the analyzers, and a separate source of air 113 is available for cleaning the transfer lines between analyses. The stepping valves 66, 90, and all other components of the system that are susceptible of control in the automated operation of the system are connected to a common controller 114 such as a computer, a programmable logic controller, or a segment of the main control system of the utility as a whole.

The monitoring of localized catalyst activity with the use of the modules described above can be performed while the SCR unit is in full operation, and is preferably performed while the unit is operating at full load. The typical SCR unit has either two, three, or four catalyst bed layers, each layer being approximately 40 to 60 square feet (3.7 to 5.5 square meters) in lateral area and approximately 3 feet (1 meter) in depth. A typical gas velocity through an SCR unit is approximately 15 feet per second (4.6 meters per second) at an operating temperature of approximately 700° F. (370° C.). A presently preferred module area is a section that is square in shape with each side measuring 2 feet (0.61 meter) in length. The amount of ammonia fed to the module to pass through the catalyst area covered by the module will be any amount that achieves a molar excess relative to the $NO_x$ entering the catalyst at that area. The amount of $NO_x$ entering the area is readily determined by analysis of a sample drawn the inlet sampling probe, thereby allowing a determination of the appropriate amount of ammonia feed. As noted above, molar ratios in excess of 1.0 are preferred, and molar ratios of about 1.2 or greater are more preferred. In a presently preferred method, a mixture of ammonia and air at an air:ammonia volume ratio of 20:5 is fed at a rate of 0.08 lb/mm (0.36 g/min) upstream of the first catalyst layer. For a multi-layer catalyst system, the optimal amount of ammonia will vary with the layer that the module is positioned to monitor.

It is further preferred that the reactions in the module be allowed to stabilize before monitoring data is taken. The ammonia feed will thus be allowed to continue for several minutes, perhaps 10 to 20 minutes, following its initiation, before the resulting data is used for activity monitoring purposes. Variations of these procedures will be made at the discretion of the operator according to the needs of the particular system. The optimum procedure for any system will be readily determinable by routine tests that are within the skill of the average engineer or system operator.

EXAMPLE

An example of a three-layer SCR unit is one that has flue gas flowing through the unit at a space velocity of 2,500 $hour^{-1}$ (the volumetric flow rate of the gas at standard temperature and pressure divided by the catalyst volume) and a linear gas velocity of 15 ft/sec (4.6 m/sec), and whose inlet $NO_x$ level is 0.41 lb/10$^6$ Btu (300 ppm at 3% $O_2$), whose inlet $NH_3/NO_x$ mole ratio is 0.9, and whose temperature is 700° F. (370° C.). The gas flowing across the individual catalyst layers has the following composition parameters:

|  |  | Bed No.: | | |
|---|---|---|---|---|
|  |  | 1 | 2 | 3 |
| Inlet: | mole ratio $NH_3/NO_x$ | 0.90 | 0.47 | 0.7 |
|  | ppm $NO_x$ | 300 | 57 | 32 |
|  | moles/min $NO_x$ | 0.0013 | 0.0002 | 0.0001 |
| Outlet: | mole ratio $NH_3/NO_x$ | 0.47 | 0.07 |  |
|  | ppm $NO_x$ | 57 | 32 | 30 |
|  | ppm $NH_3$ slip | 26.63 | 2.28 | 0.00 |
|  | $\Delta NO_x$ (%) | 81 | 43 | 8 |

With modules on each of the three layers, each module being 2 feet square (0.4 square meter), the ammonia added to the module in each layer is as follows:

|  |  | Module on Bed No.: | | |
|---|---|---|---|---|
|  |  | 1 | 2 | 3 |
| Added $NH_3$: | moles/min | 0.0004 | 0.0003 | 0.0002 |
|  | lb/min | 0.006 | 0.005 | 0.003 |
|  | cc/min | 1,418 | 1,035 | 610 |

The foregoing is offered primarily for purposes of illustration. Further modifications, substitutions, and variations that still utilize the central concepts of the invention will be readily apparent to those skilled in the art.

What is claimed is:

1. A test module for evaluating localized catalytic activity in a selected section of a solid catalyst layer in a selective catalytic $NO_x$ reduction (SCR) unit, said test module comprising:
   first and second sampling probes, means for mounting said first and second sampling probes to said SCR unit upstream and downstream, respectively, of said catalyst section, and means for drawing samples of gas through said first and second sampling probes for analysis;
   a reductant supply probe, means for mounting said reductant supply probe to said SCR unit upstream of said catalyst section at a location causing reductant from said reductant supply probe to selectively strike said catalyst section, and means for supplying reductant to said reductant supply probe; and
   barrier walls forming a lateral enclosure sized to encircle said catalyst section and to thereby prevent reductant flow from said reductant supply probe from diverging from said catalyst section.

2. The test module of claim 1 wherein said barrier walls enclose a lateral area of from about 0.1 m$^2$ to about 1 m$^2$.

3. The test module of claim 1 wherein said barrier walls enclose a lateral area of from about 0.2 m$^2$ to about 0.5 m$^2$.

4. A test module for evaluating localized catalytic activity in a selected section of a solid catalyst layer in a selective catalytic $NO_x$ reduction (SCR) unit, said test module comprising:
   first and second sampling probes, means for mounting said first and second sampling probes to said SCR unit upstream and downstream, respectively, of said catalyst section, and means for drawing samples of gas through said first and second sampling probes for analysis; and
   a reductant supply probe, a support structure for mounting said first and second sampling probes and said reductant supply probe to said SCR unit upstream of said catalyst section at a location causing reductant from said reductant supply probe to selectively strike said catalyst section, and means for supplying reductant to said reductant supply probe; and
   means for moving said support structure relative to said solid catalyst layer.

5. A test module for evaluating localized catalytic activity in a selected section of a solid catalyst layer in a selective catalytic $NO_x$ reduction (SCR) unit, said test module comprising:
   first and second sampling probes, means for mounting said first and second sampling probes to said SCR unit upstream and downstream, respectively, of said catalyst section, and means for drawing samples of gas through said first and second sampling probes for analysis;
   a reductant supply probe, means for mounting said reductant supply probe to said SCR unit upstream of said catalyst section at a location causing reductant from said reductant supply probe to selectively strike said catalyst section, and means for supplying reductant to said reductant supply probe; and
   a temperature sensor and means for mounting said temperature sensor to said SCR unit at a location whose temperature will be at least approximately equal to the temperature of said catalyst section,
   wherein said means for mounting said first and second sampling probes, said reductant supply probe, and said temperature sensor comprise a support structure, and said test module further comprises means for moving said support structure relative to said solid catalyst layer.

6. The test module of claims 1, 4, or 5 further comprising a portable $NO_x$ analyzer and means for mounting said analyzer to said first and second sampling probes.

7. The test module of claims 1, 4, or 5 wherein said selected section and said catalyst section have lateral areas, and the ratio of said lateral area of said selected section to said lateral area of said catalyst layer is about 0.25 or less.

8. The test module of claims 1, 4, or 5 wherein said selected section and said catalyst section have lateral areas, and the ratio of said lateral area of said selected section to said lateral area of said catalyst layer is about 0.1 or less.

9. A method for monitoring localized catalyst activity in a selective catalytic $NO_x$ reduction (SCR) unit in which a $NO_x$-containing gas stream is passing at a known area velocity through a body of catalyst arranged in a layer that is oriented transverse to said $NO_x$-containing gas stream, said method comprising:
   (a) feeding reductant to a selected, laterally delineated, section of said body of catalyst through a reductant supply probe upstream of, and selectively directed to, said selected section, to achieve a reductant:$NO_x$ mole ratio of about 1.2 or greater in said $NO_x$-containing gas stream entering said selected section;
   (b) drawing samples of said $NO_x$-containing gas stream from sites upstream and downstream of said selected section and analyzing said samples for a difference in $NO_x$ content between said samples; and
   (c) from said difference in $NO_x$ content and said area velocity, determining a value representative of the catalyst activity of the catalyst in said selected section.

10. The method of claim 9 wherein said reductant is ammonia gas.

11. The method of claim 9 wherein said reductant is aqueous urea.

12. The method of claim 9 further comprising detecting the temperature of said $NO_x$-containing gas stream passing through said selected section.

13. The method of claim 9 further comprising detecting the velocity of said $NO_x$-containing gas stream passing through said selected section.

14. The method of claim 9 comprising performing steps (a), (b), and (c) at a plurality of mutually distinct, laterally delineated sections of said body of catalyst and determining a value representative of the catalyst activity of the catalyst in each of said sections.

15. The method of claim 9 wherein said $NO_x$-containing gas stream is passing through a plurality of bodies of catalyst arranged in separate layers oriented transverse to said $NO_x$-containing gas stream, said method comprising performing steps (a), (b), and (c) at a plurality of mutually distinct, laterally delineated catalyst sections in different layers and determining a value representative of the catalyst activity of the catalyst in each of said sections.

16. The method of claim 9 wherein step (b) comprises drawing said samples through sampling probes and step (c) comprises detecting said temperature by a temperature sensing probe, and said sampling probes, said reductant supply probe, and said temperature sensing probe are mounted to a support that is movable relative to said solid catalyst layer, thereby permitting use of said sampling probes, reductant supply probe, and temperature sensing probe at a plurality of selected catalyst sections in sequence.

17. A method for monitoring localized catalyst activity in a selective catalytic $NO_x$ reduction (SCR) unit in which a NON-containing gas stream is passing at a known area velocity through a body of catalyst arranged in a layer that is oriented transverse to said $NO_x$-containing gas stream, said method comprising:
(a) feeding reductant to a selected, laterally delineated, section of said body of catalyst through a reductant supply probe upstream of, and selectively directed to, said selected section, to achieve a molar excess of reductant over $NO_x$ in said $NO_x$-containing gas stream entering said selected section;
(b) drawing samples of said $NO_x$-containing gas stream from sites upstream and downstream of said selected section and analyzing said samples for a difference in NOx content between said samples;
(c) from said difference in $NO_x$ content and said area velocity, determining a value representative of the catalyst activity of the catalyst in said selected section; and analyzing said samples for $O_2$ content.

18. A method for monitoring localized catalyst activity in a selective catalytic $NO_x$ reduction (SCR) unit in which a $NO_x$-containing gas stream is passing at a known area velocity through a body of catalyst arranged in a layer that is oriented transverse to said $NO_x$-containing gas stream, said method comprising:
(a) feeding reductant to a selected, laterally delineated, section of said body of catalyst through a reductant supply probe upstream of, and selectively directed to, said selected section, to achieve a molar excess of reductant over $NO_x$ in said $NO_x$-containing gas stream entering said selected section;
(b) drawing samples of said $NO_x$-containing gas stream through sampling probes from sites upstream and downstream of said selected section and analyzing said samples for a difference in $NO_x$ content between said samples, said sampling probes and said reductant supply probe being mounted to a support that is movable relative to said solid catalyst layer, said movable support permitting use of said sampling probes and said reductant supply probe at a plurality of selected catalyst sections in sequence; and
(c) from said difference in $NO_x$ content and said area velocity, determining a value representative of the catalyst activity of the catalyst in said selected section.

19. The method of claims 9, 17, or 18 wherein said selected section of said body of catalyst occupies a laterally delineated area of from about 0.1 m² to about 1 m².

20. The method of claims 9, 17, or 18 wherein said 2 selected section of said body of catalyst occupies a laterally delineated area of from about 0.2 m² to about 0.5 m².

21. The method of claims 9, 17, or 18 wherein said selected section and said catalyst section have lateral areas, and the ratio of said lateral area of said selected section to said lateral area of said body of catalyst is about 0.25 or less.

22. The method of claims 9, 17, or 18 wherein said selected section and said catalyst section have lateral areas, and the ratio of said lateral area of said selected section to said lateral area of said body of catalyst is about 0.1 or less.

23. A selective catalytic $NO_x$ reduction unit with on-line monitoring of localized catalyst activity, said unit comprising:
a flow-through reaction vessel having a flow direction therethrough and comprising a body of solid catalyst arranged therein in a layer transverse to said flow direction;
an inlet sampling probe and an outlet sampling probe mounted inside said reaction vessel upstream and downstream, respectively, of a selected section of said body of catalyst at locations such that samples of gas drawn through said sampling probes have the same composition as gas entering and leaving said selected section, respectively, and means for drawing samples of gas through said inlet and outlet sampling probes and for analyzing samples so drawn for $NO_x$ content;
a reductant supply probe mounted inside said reaction vessel upstream of said selected section to selectively direct reductant to said selected section;
means for analyzing said samples for $O_2$ content; and
a data processor for receiving a signal representative of a difference in $NO_x$ content between samples of gas drawn through said inlet and outlet sampling probes, and for determining from said signal and from the area velocity of gas through said reaction vessel a value representative of the catalyst activity of the catalyst in said selected section.

24. The selective catalytic $NO_x$ reduction unit of claim 23 further comprising a temperature sensor mounted to said reaction vessel at a location whose temperature is substantially equal to that of gas flowing through said selected section.

25. The selective catalytic $NO_x$ reduction unit of claim 24 comprising a plurality of monitoring modules, each module comprising a single pair of inlet and outlet sampling probes, a single reductant supply probe, and a single temperature sensor, each module feeding reductant to and drawing samples from a laterally delineated section of said layer of catalyst that is distinct from sections so fed and drawn from by all other modules.

26. The selective catalytic $NO_x$ reduction unit of claim 23 comprising a plurality of monitoring modules, each module comprising a single pair of inlet and outlet sampling probes and a single reductant supply probe, each module feeding reductant to and drawing samples from a laterally delineated section of said layer of catalyst that is distinct from sections so fed and drawn from by all other modules.

27. The selective catalytic $NO_x$ reduction unit of claim 26 wherein said modules are positioned at distinct laterally delineated sections of a single layer of said body of catalyst.

28. The selective catalytic $NO_x$ reduction unit of claim 26 wherein said flow-through reaction vessel comprises a plurality of layers of said body of solid catalyst, and said modules are distributed among different layers.

29. The selective catalytic $NO_x$ reduction unit of claims 27 or 28 further comprising a common source of reductant for all of said modules.

30. The selective catalytic $NO_x$ reduction unit of claim 26 further comprising:
 a first stepping valve having a plurality of ports, each port communicating with the reductant supply probe of a different module;
 a second stepping valve having a plurality of pairs of ports, each pair communicating with the inlet and outlet sampling probes, respectively, of a different module; and
 means for advancing said first and second stepping valves in coordinated manner to feed reductant to, and draw samples of gas from, each of said modules.

31. The selective catalytic $NO_x$ reduction unit of claim 23 further comprising a reductant injection grid mounted inside said reaction vessel between said reductant supply probe and said catalyst section.

32. The selective catalytic $NO_x$ reduction unit of claim 23 further comprising an air inlet mounted inside said reaction vessel upstream of said catalyst section at a location causing air from said air inlet to strike said catalyst section.

33. A selective catalytic $NO_x$ reduction unit with on-line monitoring of localized catalyst activity, said unit comprising:
 a flow-through reaction vessel having a flow direction therethrough and comprising a body of solid catalyst arranged therein in a layer transverse to said flow direction;
 an inlet sampling probe and an outlet sampling probe mounted inside said reaction vessel upstream and downstream, respectively, of a selected section of said body of catalyst at locations such that samples of gas drawn through said sampling probes have the same composition as gas entering and leaving said selected section, respectively, and means for drawing samples of gas through said inlet and outlet sampling probes and for analyzing samples so drawn for $NO_x$ content;
 a reductant supply probe mounted inside said reaction vessel upstream of said selected section to selectively direct reductant to said selected section;
 barrier walls forming a lateral enclosure encircling said catalyst section and arranged to prevent ammonia flow from said reductant supply probe from diverging from said catalyst section; and
 a data processor for receiving a signal representative of a difference in $NO_x$ content between samples of gas drawn through said inlet and outlet sampling probes, and for determining from said signal and from the area velocity of gas through said reaction vessel a value representative of the catalyst activity of the catalyst in said selected section.

34. The selective catalytic $NO_x$ reduction unit of claim 33 further comprising a static mixer mounted to said reaction vessel between said ammonia supply probe and said catalyst section.

35. The selective catalytic $NO_x$ reduction unit of claim 33 further comprising a gas flow guide arranged to direct gas entering said catalyst section to a substantially parallel flow direction that is substantially perpendicular to said layer of solid catalyst.

36. A selective catalytic $NO_x$ reduction unit with on-line monitoring of localized catalyst activity, said unit comprising:
 a flow-through reaction vessel having a flow direction therethrough and comprising a body of solid catalyst arranged therein in a layer transverse to said flow direction;
 an inlet sampling probe and an outlet sampling probe mounted inside said reaction vessel upstream and downstream, respectively, of a selected section of said body of catalyst at locations such that samples of gas drawn through said sampling probes have the same composition as gas entering and leaving said selected section, respectively, and means for drawing samples of gas through said inlet and outlet sampling probes and for analyzing samples so drawn for $NO_x$ content;
 a reductant supply probe mounted inside said reaction vessel upstream of said selected section to selectively direct reductant to said selected section; and
 a data processor for receiving a signal representative of a difference in $NO_x$ content between samples of gas drawn through said inlet and outlet sampling probes, and for determining from said signal and from the area velocity of gas through said reaction vessel a value representative of the catalyst activity of the catalyst in said selected section;
wherein said inlet and outlet sampling probes and said reductant supply probe are mounted to said reaction vessel through a support structure, and said unit further comprises means for moving said support structure relative to said layer of solid catalyst.

37. A selective catalytic $NO_x$ reduction unit with on-line monitoring of localized catalyst activity, said unit comprising:
 a flow-through reaction vessel having a flow direction therethrough and comprising a body of solid catalyst arranged therein in a layer transverse to said flow direction;
 an inlet sampling probe and an outlet sampling probe mounted inside said reaction vessel upstream and downstream, respectively, of a selected section of said body of catalyst at locations such that samples of gas drawn through said sampling probes have the same composition as gas entering and leaving said selected section, respectively, and means for drawing samples of gas through said inlet and outlet sampling probes and for analyzing samples so drawn for $NO_x$ content;
 a reductant supply probe mounted inside said reaction vessel upstream of said selected section to selectively direct reductant to said selected section;
 a temperature sensor mounted to said reaction vessel at a location whose temperature is substantially equal to that of gas flowing through said selected section; and
 a data processor for receiving a signal representative of a difference in $NO_x$ content between samples of gas drawn through said inlet and outlet sampling probes, and for determining from said signal and from the area velocity of gas through said reaction vessel a value representative of the catalyst activity of the catalyst in said selected section;
wherein said inlet and outlet sampling probes, said reductant supply probe, and said temperature sensor are mounted to said reaction vessel through a support structure, and said unit further comprises means for moving said support structure relative to said layer of solid catalyst.

38. The selective catalytic $NO_x$ reduction unit of claims 23, 33, 36 or 37 wherein said selected section and said catalyst section have lateral areas, and the ratio of said lateral area of said selected section to said lateral area of said layer of catalyst is about 0.25 or less.

39. The selective catalytic $NO_x$ reduction unit of claims 23, 33, 36, or 37 wherein said selected section and said catalyst section have lateral areas, and the ratio of said lateral area of said selected section to said lateral area of said layer of catalyst is about 0.1 or less.

* * * * *